(12) United States Patent
Abdur-Rashid et al.

(10) Patent No.: US 7,777,083 B2
(45) Date of Patent: Aug. 17, 2010

(54) IRIDIUM CATALYSTS FOR CATALYTIC HYDROGENATION

(75) Inventors: Kamaluddin Abdur-Rashid, Mississauga (CA); Rongwei Guo, Mississauga (CA); Xuanhua Chen, Mississauga (CA); Wenli Jia, Mississauga (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 91 days.

(21) Appl. No.: 12/130,039

(22) Filed: May 30, 2008

(65) Prior Publication Data

US 2008/0300430 A1 Dec. 4, 2008

Related U.S. Application Data

(60) Provisional application No. 60/941,018, filed on May 31, 2007.

(51) Int. Cl.
*C07C 29/141* (2006.01)
*C07C 29/145* (2006.01)
*C07C 35/06* (2006.01)
*C07C 35/08* (2006.01)

(52) U.S. Cl. .......... 568/814; 568/834; 568/838; 568/881; 568/883; 568/884; 568/885

(58) Field of Classification Search ............ 568/814
See application file for complete search history.

(56) References Cited

U.S. PATENT DOCUMENTS

2004/0015017 A1* 1/2004 Rautenstrauch et al. ..... 564/490

2005/0107638 A1* 5/2005 Abdur-Rashid ............. 564/489

OTHER PUBLICATIONS

Dörwald, Side Reactions in Organic Synthesis, IX and 1-15 (2005).*
Bianchini et al., Organometallics (1998), 17, p. 3308-3310.*
Bianchini et al., J. of Molecular Catalysis A: Chemical (1998), 132, p. 13-19.*
Bianchini et al., Organometallics (1995), 14, p. 1489-1502.*
Bianchini et al., J. American Chemical Society (1990), 112, p. 9190-9197.*
Bi, Siwei, et al., "Theoretical investigation on the mechanisms of transfer hydrogenation of ketones catalyzed by iridium complexes", Journal of Organometallic Chemistry, 2008, vol. 693, No. 4, pp. 633-638.
Choualeb, Aldjia, et al., "Hemilabile Pincer-Type Hydride Complexes of Iridium", Organometallics, 2007, vol. 26, No. 21, pp. 5224-5229.
Choualeb, Aldjia, et al., "Hydridic Rhenium Nitrosyl Complexes with Pincer-Type PNP Ligands", Organometallics, 2007, vol. 26, No. 14, pp. 3509-3515.
Chen, Xuanhua, et al., "Highly active iridium catalysts for the hydrogenation of ketones and aldehydes", Dalton Transactions, 2009, No. 8, pp. 1407-1410.
Clarke, Zaheer E., et al., "A Family of Active Iridium Catalysts for Transfer Hydrogenation of Ketones", Organometallics, 2006, vol. 25, No. 17, pp. 4113-4117.

* cited by examiner

*Primary Examiner*—Brian J Davis
(74) *Attorney, Agent, or Firm*—Bereskin & Parr LLP/S.E.N.C.R.L., s.r.l.; Michael Fenwick

(57) ABSTRACT

A process for the reduction of compounds comprising one or more carbon-oxygen (C=O) double bonds, to provide the corresponding alcohol, comprising contacting the compound with hydrogen gas at a pressure greater than 3 atm and a catalyst comprising an iridium aminodiphosphine complex.

33 Claims, 2 Drawing Sheets

IRIDIUM CATALYSTS FOR CATALYTIC HYDROGENATION

FIELD OF THE APPLICATION

The present application relates to the field of catalytic hydrogenation, in which a catalytic system comprising an iridium aminodiphosphine complex and hydrogen gas is used for the reduction of compounds containing a carbon-oxygen (C=O) double bond in the presence of a base.

BACKGROUND OF THE APPLICATION

Catalytic hydrogenation is a fundamental reaction in chemistry, and is used in a large number of chemical processes. Catalytic hydrogenation of ketones and aldehydes are useful and indispensable processes for the synthesis of alcohols, which are valuable end products and precursor chemicals in the pharmaceutical, agrochemical, flavor, fragrance, material and fine chemical industries.[1]

To achieve a catalytic hydrogenation transformation in the reduction of ketones and aldehydes, molecular hydrogen ($H_2$) is used. However, for the hydrogenation process to proceed, a catalyst or catalytic system is needed to activate the molecular hydrogen.

Noyori and co-workers developed the versatile $RuCl_2(PR_3)_2$(diamine) and $RuCl_2$(diphosphine)(diamine) hydrogenation catalyst system that are highly effective for the hydrogenation of ketones.[2] It was subsequently discovered that the Noyori catalysts were effective for the reductive hydrogenation of imines to amines.[3] It has been determined that in the presence of a base and hydrogen gas that the active catalyst species are ruthenium dihydride species of the type $RuH_2(PR_3)_2$(diamine) and $RuH_2$(diphosphine)(diamine).[3,4] The mechanistic investigation included the synthesis, isolation and characterization of the highly reactive amidoaminohydrido species that activates hydrogen to regenerate the active dihydride catalysts.[4] It was clearly demonstrated that the carbonyl molecular recognition motif of these catalysts is the mutually cis N—H and Ru—H moieties in the dihydride catalysts, which facilitate hydrogenation through an outer-sphere hydrogen transfer process.[4]

The synthesis and characterization of a series of iridium hydride species has recently been reported.[5] This series included $IrH_2Cl[(^iPr_2PC_2H_4)_2NH]$ (1), $IrH_3[(^iPr_2PC_2H_4)_2NH]$ (2) and $IrH_2[(^iPr_2PC_2H_4)_2N]$ (3).[5] It was demonstrated that 2 and 3 are very active catalysts for the base-free transfer hydrogenation of ketones in 2-propanol, while 1 is air-stable and inactive as a catalyst in the absence of a base. It was also reported that 3 rapidly formed 2 upon exposure of a solution of 2 to hydrogen gas. Further it was reported that 1, 2 and 3 could not effect the hydrogenation of ketones in the presence of $H_2$ at 3 atm in benzene at room temperature.[5]

SUMMARY OF THE APPLICATION

It has now been found that an iridium aminodiphosphine complex and hydrogen gas are efficient for the catalytic reductive hydrogenation of compounds containing a carbon-oxygen (C=O) double bond under certain conditions.

Therefore, the present application includes a method for the reduction of compounds comprising one or more carbon-oxygen (C=O) double bonds comprising contacting the compound with hydrogen gas and a catalyst comprising an iridium aminodiphosphine complex, wherein the hydrogen gas is used at a pressure greater than 3 atmospheres (atm).

In an embodiment of the application, the compound comprising a carbon-oxygen (C=O) is a compound of formula (I):

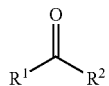

(I)

wherein, $R^1$ and $R^2$ each simultaneously or independently are selected from H, aryl, $C_{1-20}$alkyl, $C_{2-20}$alkenyl, $C_{3-20}$cycloalkyl and heteroaryl, said latter 5 groups being optionally substituted, or $R^1$ and $R^2$ are linked to form an optionally substituted ring;

wherein heteroaryl is a mono- bi or tricyclic heteroaromatic radical containing from 5 to 14 atoms, of which 1-5 atoms is a heteromoiety selected from S, O, N, NH and $NC_{1-6}$alkyl and wherein the optional substituents are selected from one or more of =O, halo, OH, $NH_2$, $OR^c$, $NR^c_2$ and $R^c$, in which $R^c$ is selected from $C_{1-6}$alkyl, $C_{2-6}$alkenyl, $C_{3-10}$cycloalkyl and aryl and one or more of the carbon atoms in the alkyl, alkenyl cycloalkyl and aryl groups is optionally replaced with a heteromoiety selected from O, S, N, NH, $NC_{1-6}$alkyl, P and Si and one or more of the hydrogen atoms in the alkyl, alkenyl, cycloalkyl and aryl groups is optionally replaced with F.

Reduction of compounds of formula I using the method of the application provides the corresponding alcohols of formula (I'):

(I')

wherein $R^1$ and $R^2$ are defined as in formula (I).

In one embodiment, the methods of the application are characterized by the use of a catalytic system comprising an iridium precursor complex with a tridentate aminodiphosphine ligand in the presence of a base and hydrogen gas at greater than 3 atm, in which the iridium precursor complex is of the formula (II):

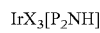

$IrX_3[P_2NH]$ (II)

wherein

X may be the same or different and are selected from hydrogen and any anionic ligand;

$[P_2NH]$ represents a tridentate aminodiphosphine ligand of formula (III):

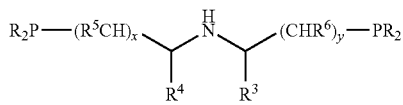

(III)

in which $R^3$ to $R^6$ simultaneously or independently are selected from of H, $C_{1-20}$alkyl, $C_{2-20}$alkenyl, $C_{3-20}$cycloalkyl and aryl, said latter 4 groups being optionally substituted, or two adjacent or geminal $R^3$, $R^4$, $R^5$ or $R^6$ groups are bonded together to form an optionally substituted ring;

x and y are, simultaneously or independently, equal to 0, 1, 2, 3 or 4; and

R is simultaneously or independently selected from H, $C_{1-20}$alkyl, aryl and $C_{2-20}$alkenyl, $OR^d$ and $NR^d{}_2$, said latter 5 groups being optionally substituted, or the R groups on the same P atom are linked together to form an optionally substituted monocyclic or polycyclic, saturated, unsaturated and/or aromatic ring system having 4 or more atoms, including the phosphorous atom to which said R groups are bonded, and in which one or more carbon atoms in said ring system is optionally replaced with a heteromoiety selected from O, S, N, NH, $NC_{1-6}$alkyl and Si;

the optional substituents are selected from one or more of halo, OH, $NH_2$, $OR^d$, $NR^d{}_2$ and $R^d$;

$R^d$ is selected from $C_{1-6}$alkyl, $C_{2-6}$alkenyl, $C_{3-10}$cycloalkyl and aryl, wherein one or more of the carbon atoms in the alkyl, alkenyl, cycloalkyl and aryl groups is optionally replaced with a heteromoiety selected from O, S, N, NH, $NC_{1-6}$alkyl and Si and one or more of the hydrogen atoms in the alkyl, alkenyl, cycloalkyl and aryl groups is optionally replaced with F, wherein the iridium precursor complex is activated in situ.

In another embodiment, the methods of the application are characterized by the use of a catalytic system comprising an iridium precursor complex with a tridentate aminodiphosphine ligand and hydrogen gas at greater than 3 atm, in which the iridium precursor complex is of the formula (IV)

$$IrH_3[P_2NH] \qquad\qquad (IV)$$

wherein

[$P_2NH$] is as defined in the formula II.

An advantage of the iridium precursor catalyst system relative to the Noyori-type ruthenium analogues is that the active iridium complex of the formula (IV) and the iridium precursor complex of the formula (II) are more stable and easily handled relative to the ruthenium dihydride and amidohydride counterparts. The enhanced stability of the iridium catalysts allows their use in a wide variety of solvents, including dichloromethane. On the contrary, the Noyori-type of catalysts are deactivated in dichloromethane.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The application will now be described in greater detail with reference to the following drawings in which.

DETAILED DESCRIPTION OF THE APPLICATION

Definitions

Figure 1:
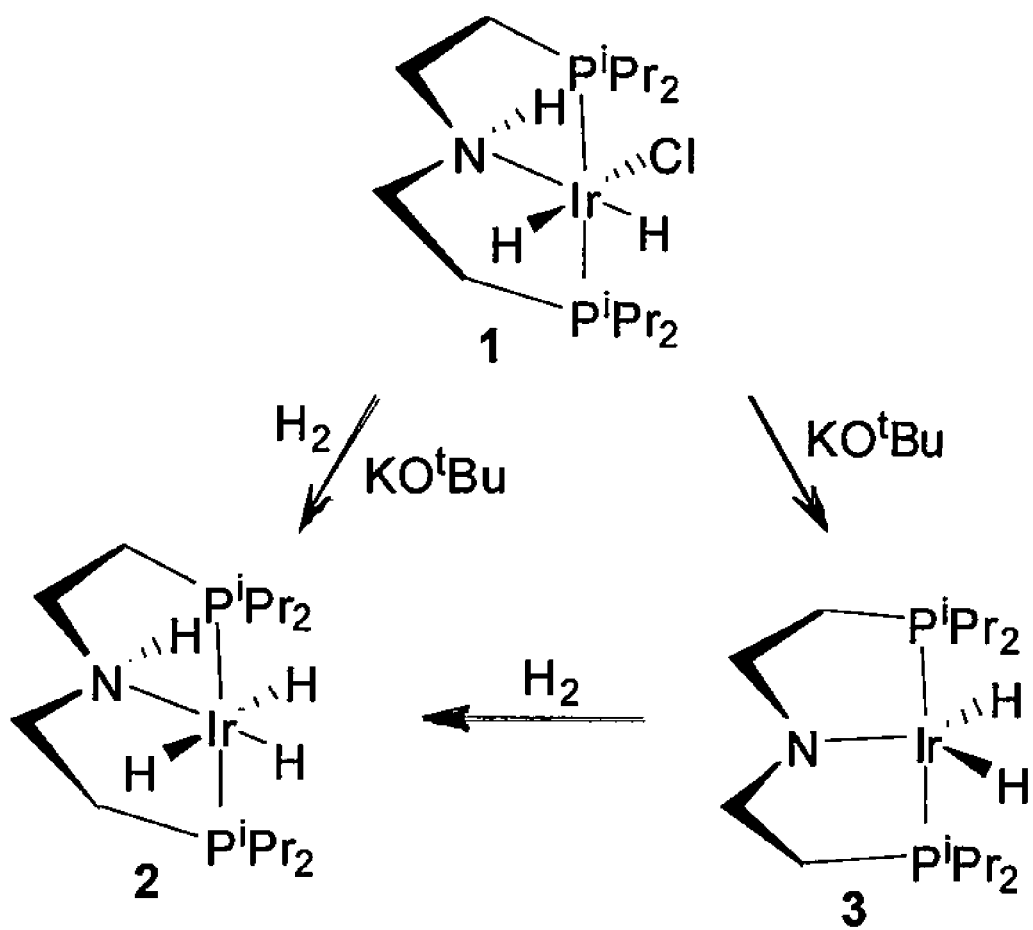
FIG. 1 is a schematic showing the activation of $IrH_2Cl$ [$(^iPr_2PC_2H_4)_2NH$] in the presence of a base and hydrogen gas.

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl groups.

The term "$C_{1-n}$alkenyl" as used herein means straight and/or branched chain, unsaturated alkyl groups containing from one to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl group.

The term "$C_{3-20}$ocycloalkyl" as used herein means a monocyclic, bicyclic or tricyclic saturated carbocylic group containing from three to twenty carbon atoms and includes cyclopropyl, cyclobutyl, cyclopentyl, cyclodecyl and the like.

The term "aryl" as used herein means a monocyclic, bicyclic or tricyclic aromatic ring system containing from 6 to 14 carbon atoms and at least 1 aromatic ring and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and from 5 to 14 atoms of which, unless otherwise specified, one, two, three, four or five are a heteromoiety independently selected from N, NH, $NC_{1-6}$alkyl, O and S and includes thienyl, furyl, pyrrolyl, pyrididyl, indolyl, quinolyl, isoquinolyl, tetrahydroquinolyl, benzofuryl, benzothienyl and the like.

The term "fluoro-substituted" with respect to any specified group as used herein means that the one or more, including all, of the hydrogen atoms in the group have been replaced with a fluorine, and includes trifluoromethyl, pentafluoroethyl, fluoromethyl and the like.

The term "halo" as used herein means halogen and includes chloro, flouro, bromo, iodo and the like.

The term "ring" or "ring system" as used herein refers to carbocycles, except where indicated that one or more carbon atoms may be replaced with heteroatom.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Methods of the Application

It has been found that tridentate aminodiphosphine ligands, when complexed with iridium, are particularly efficient catalysts for the reduction of C=O double bonds under catalytic hydrogenation conditions with hydrogen gas pressures of greater than 10 atm.

Accordingly, the present application relates to a method for the reduction of compounds comprising one or more carbon-oxygen (C=O) double bonds comprising contacting the compound with hydrogen gas and a catalyst comprising an iridium aminodiphosphine complex, wherein the hydrogen gas is used at a pressure greater than 3 atm.

The compound comprising a C=O, includes compounds having one or more C=O bonds.

In an embodiment of the application, the compound comprising a carbon-oxygen (C=O) is a compound of formula (I):

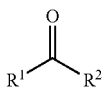

(I)

wherein, $R^1$ and $R^2$ each simultaneously or independently are selected from H, aryl, $C_{1-20}$alkyl, $C_{2-20}$alkenyl, $C_{3-20}$cycloalkyl and heteroaryl, said latter 5 groups being optionally substituted, or $R^1$ and $R^2$ are linked to form an optionally substituted ring;

wherein heteroaryl is a mono- bi or tricyclic heteroaromatic radical containing from 5 to 14 atoms, of which 1-5 atoms is a heteromoiety selected from S, O, N, NH and $NC_{1-6}$ alkyl and wherein the optional substituents are selected from one or more of =O, halo, OH, $NH_2$, $OR^c$, $NR^c_2$ and $R^c$, in which $R^c$ is selected from $C_{1-6}$alkyl, $C_{2-6}$alkenyl, $C_{3-10}$cycloalkyl and aryl and one or more of the carbon atoms in the alkyl, alkenyl cycloalkyl and aryl groups is optionally replaced with a heteromoiety selected from O, S, N, NH, $NC_{1-6}$alkyl, P and Si and one or more of the hydrogen atoms in the alkyl, alkenyl, cycloalkyl and aryl groups is optionally replaced with F.

Reduction of compounds of formula I using the method of the application provides the corresponding alcohols of formula (I'):

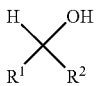

(I')

wherein $R^1$ and $R^2$ are defined as in formula (I).

Since $R^1$ and $R^2$ may be different, it is hereby understood that the final product, of formula (I'), may be chiral, thus possibly consisting of a practically pure enantiomer or of a mixture of stereoisomers, depending on the nature of the catalyst used in the process.

In one embodiment, the methods of the application are characterized by the use of a catalytic system comprising an iridium precursor complex with a tridentate aminodiphosphine ligand in the presence of a base and hydrogen gas at greater than 3 atm, in which the iridium precursor complex is of the formula (II):

$$IrX_3[P_2NH] \quad (II)$$

wherein

X may be the same or different and are selected from hydrogen and any anionic ligand;

[$P_2NH$] represents a tridentate aminodiphosphine ligand of formula (III):

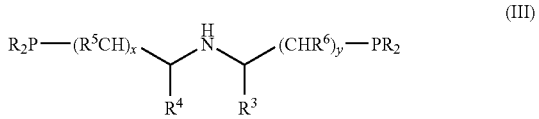

(III)

in which $R^3$ to $R^6$ simultaneously or independently are selected from of H, $C_{1-20}$alkyl, $C_{2-20}$alkenyl, $C_{3-20}$cycloalkyl and aryl, said latter 4 groups being optionally substituted, or two adjacent or geminal $R^3$, $R^4$, $R^5$ or $R^6$ groups are bonded together to form an optionally substituted ring;

x and y are, simultaneously or independently, equal to 0, 1, 2, 3 or 4; and

R is simultaneously or independently selected from H, $C_{1-20}$alkyl, aryl and $C_{2-20}$alkenyl, $OR^d$ and $NR^d_2$, said latter 5 groups being optionally substituted, or the R groups on the same P atom are linked together to form an optionally substituted monocyclic or polycyclic, saturated, unsaturated and/or aromatic ring system having 4 or more atoms, including the phosphorous atom to which said R groups are bonded, and in which one or more carbon atoms in said ring system is optionally replaced with a heteromoiety selected from O, S, N, NH, $NC_{1-6}$alkyl and Si;

the optional substituents are selected from one or more of halo, OH, $NH_2$ $OR^d$, $NR^d_2$ and $R^d$;

$R^d$ is selected from $C_{1-6}$alkyl, $C_{2-6}$alkenyl, $C_{3-10}$cycloalkyl and aryl, wherein one or more of the carbon atoms in the alkyl, alkenyl, cycloalkyl and aryl groups is optionally replaced with a heteromoiety selected from O, S, N, NH, $NC_{1-6}$alkyl and Si and one or more of the hydrogen atoms in the alkyl, alkenyl, cycloalkyl and aryl groups is optionally replaced with F.

In an embodiment of the present application, the tridentate ligand of formula III includes those in which $R^3$ to $R^6$ simultaneously or independently are selected from H, $C_{1-10}$alkyl, $C_{2-10}$alkenyl, $C_{3-10}$cycloalkyl and aryl, said latter 4 groups being optionally substituted, or two adjacent or geminal $R^3$, $R^4$, $R^5$ or $R^6$ groups are bonded together to form an optionally substituted ring. In further embodiments of the application, $R^3$ to $R^6$ simultaneously or independently are selected from H, $C_{1-4}$alkyl, $C_{2-4}$alkenyl, $C_{3-6}$cycloalkyl and aryl, said latter 4 groups being optionally substituted, or two adjacent or geminal $R^3$, $R^4$, $R^5$ or $R^6$ groups are bonded together to form an optionally substituted ring, said ring containing 6 atoms, including the carbons to which said groups are attached. In further embodiments of the application $R^3$ to $R^6$ are all H. In further embodiments, the optional substitution is the replacement of one or more hydrogen atoms with fluorine.

In embodiments of the application, the tridentate ligand of formula III further includes those in which x and y are simultaneously equal to 0, 1, 2, 3 or 4. In further embodiments of the application, x and y are simultaneously equal to 0, 1 or 2. In still further embodiments of the application, x and y are simultaneously equal to 1.

In the present application, the tridentate ligand of formula III still further includes those in which R is simultaneously or independently selected from H, $C_{1-10}$alkyl, aryl and $C_{2-10}$alkenyl, said latter 3 groups being optionally substituted, or the R groups on the same P atom may be linked together to form an optionally substituted monocyclic or polycyclic ring system having 4 or more atoms, including the phosphorous atom to which said R groups are bonded, in which the rings are optionally saturated, unsaturated and/or aromatic and in which one or more carbon atoms in said monocyclic or polycyclic ring system is optionally be replaced with a heteromoiety selected from O and NH. In still further embodiments of the application, R is simultaneously or independently selected from H, $C_{1-6}$alkyl, phenyl, naphthyl and $C_{2-6}$alkenyl, said latter 3 groups being optionally substituted, or the R groups on the same P atom are optionally linked together to form an optionally substituted monocyclic, fused bicyclic, fused tricyclic, fused quadracyclic or fused pentacyclic ring system having 4-23 atoms, including the phosphorous atom to which said R groups are bonded, in which the rings are optionally saturated, unsaturated and/or aromatic and in which one or more carbon atoms in said monocyclic or polycyclic ring system is optionally replaced with a heteromoiety selected from O and NH. In yet further embodiments, the optional substitution on the R groups is the replacement of one or more hydrogen atoms with fluorine.

In an embodiment of the application, R is simultaneously $C_{1-6}$alkyl or phenyl, in particular, methyl, ethyl, propyl, isopropyl, t-butyl, sec-butyl or phenyl. In a further embodiment, R is isopropyl.

In another embodiment of the application, the two R groups on each phosphorus atom are linked to form a monocyclic saturated ring contain from 4 to 7 atoms, specifically 4-5 atoms, including the phosphorus atom to which the R groups are attached, said ring being optionally substituted with 1 to 2 substituents independently selected from fluoro-substituted-$C_{1-6}$alkyl, $C_{1-6}$alkyl, $C_{2-6}$alkenyl and aryl, specifically $C_{1-4}$alkyl, $C_{2-4}$alkenyl and phenyl, more specifically methyl or phenyl, and wherein one or two of the carbon atoms in the ring are optionally replaced with a heteromoiety selected from O, S and N—$C_{1-4}$alkyl, specifically O and N—$CH_3$. It is a further embodiment of the application, that when the two R groups on each phosphorus atom are linked to form a monocyclic ring, the optional heteromoieties or optional substituents are located at the positions alpha to the phosphorus atom.

In yet another embodiment of the present application, the two R groups on the phosphorus atom are linked to form a polycyclic ring system comprising 3, 5 or 7 rings each which are optionally fully saturated, partially unsaturated and/or aromatic and which are optionally substituted with 1 to 2 substituents independently selected from fluoro-substituted-$C_{1-6}$alkyl, $C_{1-6}$alkyl, $C_{2-6}$alkenyl and aryl, specifically $C_{1-4}$alkyl, $C_{2-4}$alkenyl and phenyl, more specifically methyl or phenyl, and wherein one or two of the carbon atoms in the ring are optionally replaced with a heteromoiety selected from O, S and N—$C_{1-4}$alkyl, specifically O and N—$CH_3$. It is a further embodiment of the application, that when the two R groups on each phosphorus atom are linked to form a polycyclic ring system, any optional heteromoieties or optional substituents are located at the positions alpha to the phosphorus atom.

Further it is an embodiment of the application that both phosphorus atoms in the compounds of Formula II are identically substituted.

According to an embodiment of the application, the optional substituents on the compounds of formula III are selected from one or more of halo, OH, $NH_2$, $OR^d$, $NR^d_2$ and $R^d$, in which $R^d$ is selected from fluoro-substituted-$C_{1-4}$alkyl, $C_{1-4}$alkyl, $C_{2-4}$alkenyl and phenyl, specifically methyl and phenyl.

The ligands X may be the same or different and are selected from hydrogen and any anionic ligand, suitably halo (for example, fluoro, chloro, bromo or iodo, specifically chloro). In an embodiment of the application, two of the X ligands are hydrogen and one is chloro.

The complexes of formula (II) can be prepared and isolated prior to their use in the process according to the general methods described in the literature (see for example, Clarke, Z. E. et al. Organometallics, 2006, 25:41113-4117) or using the methods described herein.

The catalytic system defined by formula (II) is activated in the presence of a base and hydrogen gas to form the active species in which the iridium complex is of the formula IV:

$$IrH_3[P_2NH] \quad (IV)$$

wherein
[$P_2NH$] is as defined in the formula II.

The base can be any conventional base and one can cite, as non-limiting examples, organic non-coordinating bases such as DBU, an alkaline or alkaline-earth metal carbonate, a carboxylate salt such as sodium or potassium acetate, or an alcoholate or hydroxide salt. In an embodiment of the application, the bases are the alcoholate or hydroxide salts selected from the compounds of formula $(R^7O)_2M'$ and $R^7OM''$, wherein M' is an alkaline-earth metal, M'' is an alkaline metal and $R^7$ stands for hydrogen or a linear or branched $C_{1-10}$alkyl group. In a further embodiment of the application, $R^7$ is t-butyl and M'' is potassium.

Standard catalytic hydrogenation conditions, as used herein, typically implies the mixture of the substrate with an iridium precursor complex of formula (II) in the presence of a base, with a solvent, and then treating such a mixture with a hydrogen gas at a chosen pressure and temperature or the mixture of the substrate with an iridium precursor complex of formula (IV) in the absence of a base, with a solvent, and then treating such a mixture with a hydrogen gas at a chosen pressure and temperature.

The hydrogen gas is used at a pressure of greater than 3 atm. In an embodiment of the application, the hydrogen gas is used at a pressure in the range of about 7 atm to about 13 atm, suitably at about 10 atm.

The complexes of formula (II) or (IV) can be added to the reaction medium in a large range of concentrations. As non-limiting examples, one can cite as complex concentration values those ranging from 0.1 ppm to 50,000 ppm, relative to the amount of substrate, thus representing respectively a substrate/complex (S/com) ratio of $10^7$ to 20. In an embodiment of the application, the complex concentration will be comprised between 0.1 and 1000 ppm, i.e. a S/com ratio of $10^7$ to 1000 respectively. In a further embodiment of the application, there will be used concentrations in the range of 0.5 to 100 ppm, corresponding to a S/com ratio of 10,000 to $2\times10^6$ respectively.

The base may be comprised in a relatively large range. One can cite, as non-limiting examples, ranges between 1 to 50,000 molar equivalents relative to the complex (e.g. base/complex=0.5 to 50,000), or 100 to 20,000, or even between 400 and 10,000 molar equivalents. However, it should be noted that it is also possible to add a small amount of base (e.g. base/complex=1 to 3) to achieve high yields.

In the methods of this application, the catalytic hydrogenation reaction is carried out in the presence of a solvent. A wide variety of solvents can be used for the catalytic hydrogenation. Non-limiting examples include aromatic solvents such as benzene, toluene or xylene, hydrocarbon solvents such as hexane or cyclohexane, ethers and esters such as tetrahydrofuran, diethyl ether and ethyl acetate, primary or secondary alcohols such as methanol, ethanol and isopropanol, chlorinated solvents such as dichloromethane and chloroform, or mixtures thereof.

The temperature at which the catalytic hydrogenation is carried out is suitably about 0° C. to about 100° C., more specifically in the range of 20° C. to 80° C. In an embodiment of the application, the catalytic hydrogenation is carried out at room temperature. Of course, a person skilled in the art is also able to adjust the temperature to optimize yields using methods known in the art.

The following non-limiting examples are illustrative of the present application:

EXAMPLES

The application will now be described in further details by way of the following examples, wherein the temperatures are indicated in degrees centigrade and the abbreviations have the usual meaning in the art. All the procedures described hereafter have been carried out under an inert atmosphere unless stated otherwise. All preparations and manipulations were carried out under $H_2$, $N_2$ or Ar atmospheres with the use of standard Schlenk, vacuum line and glove box techniques in dry, oxygen-free solvents.

Tetrahydrofuran (THF), diethyl ether ($Et_2O$) and hexanes were dried and distilled from sodium benzophenone ketyl. Deuterated solvents were degassed and dried over activated molecular sieves. Potassium tert-butoxide, aldehydes and ketones were supplied by Aldrich Chemical Company. NMR spectra were recorded on either a Varian Unity Inova 300 MHz spectrometer (300 MHz for $^1H$, 75 MHz for $^{13}C$ and 121.5 for $^{31}P$) or a Bruker Avance 500 Mhx DRX spectrometer. All $^{31}P$ chemical shifts were measured relative to 85% $H_3PO_4$ as an external reference. $^1H$ and $^{13}C$ chemical shifts were measured relative to partially deuterated solvent peaks but are reported relative to tetramethylsilane. The ligand $(iPr_2PC_2H_4)_2NH$ and the air stable catalyst precursor $IrH_2Cl[(iPr_2PC_2H_4)_2NH]$ are commercially available from Kanata Chemical Technologies Inc.

Example 1

Preparation of the Ligand Bis(2-(diisopropylphosphino)ethyl)amine, $(^iPr_2PC_2H_4)_2NH$ and Iridium Complexes

Example 1.1

Preparation of Bis(2-(diisopropylphosphino)ethyl)amine, $(^iPr_2PC_2H_4)_2NH$

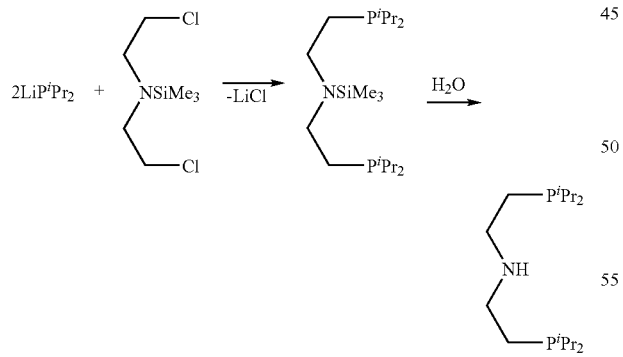

Chlorodiisopropylphosphine (11.0 g) was added in 2 g portions to a vigorously stirred suspension of lithium granules (1.5 g) in THF (30 ml) and the mixture was stirred for 3 days at room temperature. The mixture was filtered through a coarse sintered glass frit to remove excess lithium, then cooled to −80° C. and a solution of $(ClC_2H_4)_2NSiMe_3$ (7.75 g) in 10 ml of THF slowly added. The resulting suspension was allowed to slowly warm to room temperature and then refluxed for one hour. After cooling to room temperature, 15 ml of water was added and the mixture stirred for one hour. The aqueous layer was removed and another 15 ml of water and 15 ml of hexane added. The biphasic mixture was refluxed for 4 hours then cooled to room temperature. The aqueous layer was removed and the mixture evaporated to give the crude diphosphine. This was purified by distillation under vacuum. The fraction boiling at 120-140° C. was collected. Yield=9.72 g.

Example 1.2

Preparation of $IrH_2Cl[(^iPr_2PC_2H_4)_2NH]$ (1)

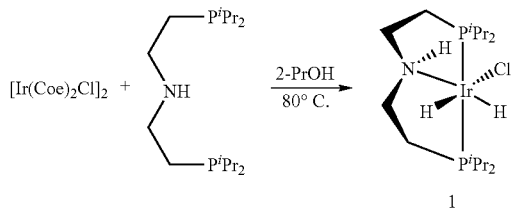

2-Propanol (3 ml) was added to a mixture of $[Ir(coe)_2Cl]_2$ (1.5 g) and $(^iPr_2PC_2H_4)_2NH$ (1.02 g) and the mixture warmed for 45 minutes at 60° C. Hexane (6 ml) was added to the cooled solution, and the resulting crystalline white solid (1) was filtered, washed with hexanes and dried under vacuum. Yield=1.52 g.

Example 1.3

Preparation of $IrH_3[(^iPr_2PC_2H_4)_2NH]$ (2)

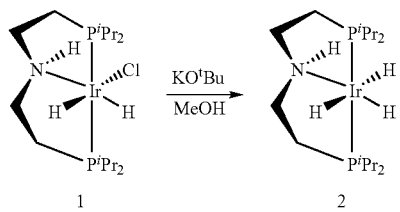

As described in Clarke, Z. E. et al. Organometallics, 2006, 25:41113-4117.

FIG. 1 shows the activation of $IrH_2Cl[(^iPr_2PC_2H_4)_2NH]$ in the presence of a base and hydrogen gas.

Example 2

Catalytic Hydrogenation of Acetophenone Using Iridium Catalyst $IrH_3[(^iPr_2PC_2H_4)_2NH]$ (2) and Iridium Precursor Complex $IrH_2Cl[(^iPr_2PC_2H_4)_2NH]$ (1)

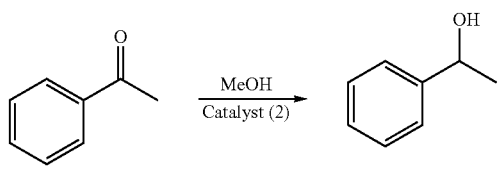

Figure 2:
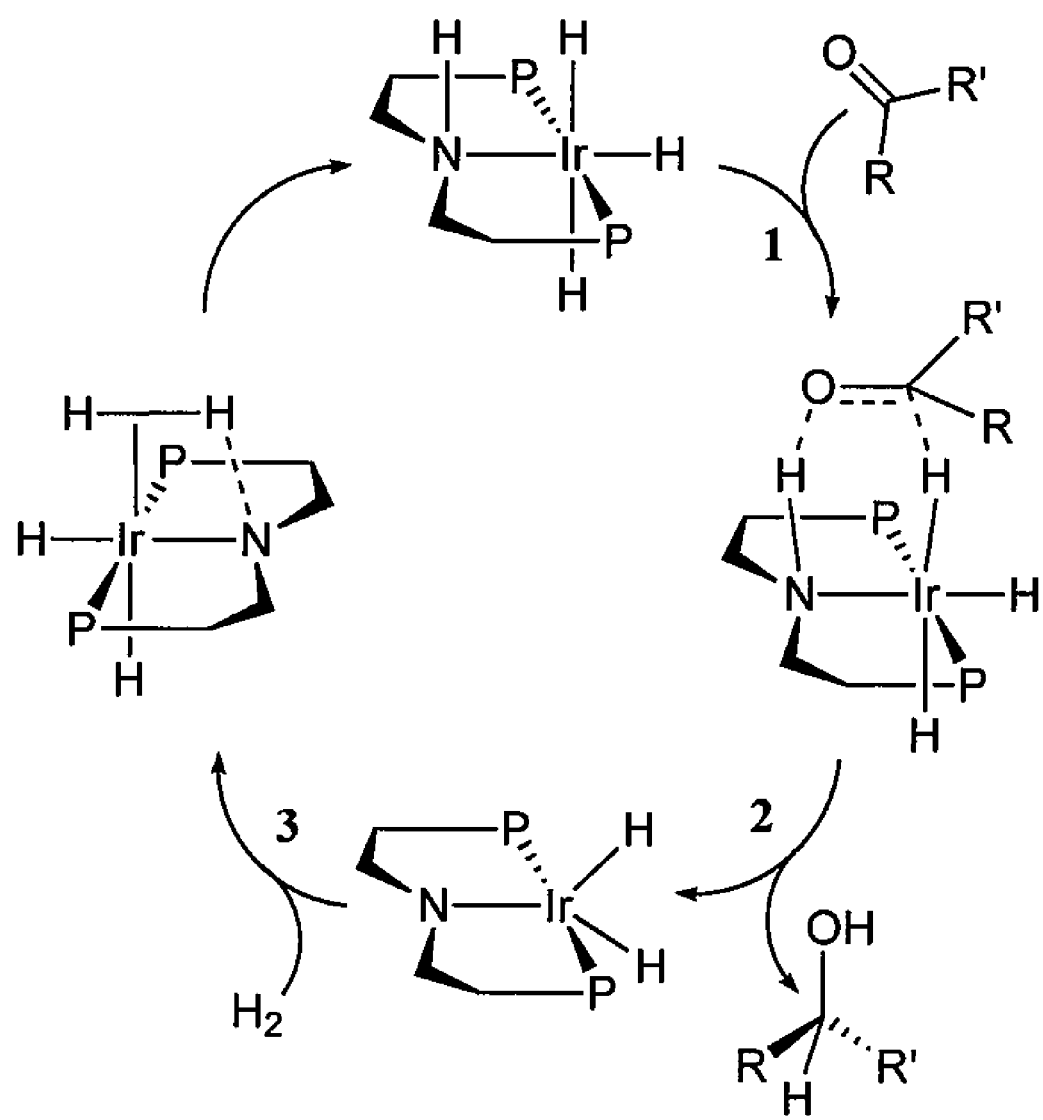
FIG. 2 is a schematic showing a proposed hydrogenation mechanism.

FIG. 2 shows a proposed hydrogenation mechanism.

Example 2.1

Catalytic Hydrogenation of Acetophenone Using IrH$_3$[($^i$Pr$_2$PC$_2$H$_4$)$_2$NH] as Catalyst A weighed amount of IrH$_3$[($^i$Pr$_2$PC$_2$H$_4$)$_2$NH] was added to a solution of acetophenone in methanol and the mixture stirred at the required temperature for the allotted time under hydrogen gas at 10 atm. The reaction progress was monitored using NMR. The solvent was removed by evaporation under reduced pressure. The results are presented in Table 1.

Example 2.2

Catalytic Hydrogenation of Acetophenone Using IrH$_2$Cl[($^i$Pr$_2$PC$_2$H$_4$)$_2$NH)] (1) as Catalyst Precursor A weighed amount of IrH$_2$Cl[($^i$Pr$_2$PC$_2$H$_4$)$_2$NH] was added to a solution of acetophenone and KO$^t$Bu (when necessary) in methanol and the mixture stirred at the room temperature under hydrogen gas at 10 atm. The reaction progress was monitored using NMR. The solvent was removed by evaporation under reduced pressure. The results are presented in Table 1.

Example 3

Catalytic Hydrogenation of Acetophenone IrH$_2$Cl[($^i$Pr$_2$PC$_2$H$_4$)$_2$NH)] (1) as Catalyst Precursor in Various Solvents A weighed amount of IrH$_2$Cl[($^i$Pr$_2$PC$_2$H$_4$)$_2$NH] (1) and KO$^t$Bu (1:10) was added to a solution of acetophenone in methanol and the mixture stirred at the room temperature for the allotted time under hydrogen gas at 10 atm. The reaction progress was monitored using NMR. The solvent was removed by evaporation under reduced pressure. The results are presented in Table 2.

Example 4

Catalytic Hydrogenation of Ketones and Aldehydes Using IrH$_2$Cl[($^i$Pr$_2$PC$_2$H$_4$)$_2$NH)] (1) as Catalyst Precursor

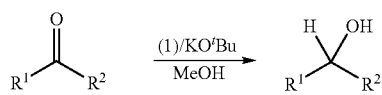

A weighed amount of IrH$_2$Cl[($^i$Pr$_2$PC$_2$H$_4$)$_2$NH] (1) and KO$^t$Bu (1:10) were added to a solution of ketone or aldehyde in methanol and the mixture stirred at the room temperature for the allotted time under hydrogen gas at 10 atm. The reaction progress was monitored using NMR. The solvent is removed by evaporation under reduced pressure. The results are presented in Table 3.

Discussion

The base-free hydrogenation of acetophenone in methanol using 2 as a catalyst and hydrogen gas (entries 1 and 2) is summarized in Table 1. The results demonstrate the effectiveness of the iridium trihydride complex as a hydrogenation catalyst. Under similar conditions 1 was totally ineffective (entry 3) as a catalyst. On the other hand the use of 1/KO$^t$Bu (1:10) as the catalyst, resulted in complete conversion of acetophenone to phenylethanol (entries 4 and 5). This clearly demonstrates that the air-stable complex 1 serves as a precursor to the active catalyst 2 in the presence of a base and hydrogen gas.

The effectiveness of this new catalytic hydrogenation system in a variety of solvents was then investigated using 1/KO$^t$Bu (1:10) as the catalyst. The results are summarized in Table 2. This shows that hydrogenation is possible in most common laboratory solvents, including dichloromethane and chloroform. Similar results were obtained using 2 as catalyst. The active ruthenium species RuH$_2$(PR$_3$)$_2$(diamine) and RuH$_2$(diphosphine)(diamine) and their amido analogues are known to rapidly form the inactive hydridochloro species RuHCl(PR$_3$)$_2$(diamine) and RuHCl(diphosphine)(diamine) in the presence of dichloromethane or chloroform.[4]

Table 3 summarizes the hydrogenation of a variety of ketones and aldehydes using 1/KO$^t$Bu as hydrogenation catalyst at room temperature. Acetophenone was converted to phenylethanol even at high substrate to catalyst ratios (entries 1-3). Benzophenone was converted to benzhydrol under similarly mild reaction conditions. Unactivated dialkyl ketones were readily converted to their respective alcohols, including sterically congested and electronically deactivated pinacolone (entry 11). Reduction of 4-tert-butylcyclohexanone resulted in a 1:2 non-thermodynamic mixture of the cis and trans alcohols, respectively. The hydrogenation of conjugated ketones was also investigated. Benzalacetone was converted to the allyl alcohol as the only detectable product, whereas hydrogenation of cyclohex-2-enone resulted in a 1:1 mixture of the allyl and saturated alcohols. Only the carbonyl group of b-ionone was reduced to give the respective alcohol. The hydrogenation of the diketone benzil formed mainly the meso alcohol (meso:rac=3:1), whereas hexane-2,5-dione resulted in only rac-2,5-hexanediol. A 6:1 mixture of endo:exo norborneol resulted from the hydrogenation of norcamphor. Hydrogenation of benzaldehyde and valeraldehyde gave their respective alcohols.

While not wishing to be limited by theory, the mild reaction conditions and the wide range of substrates converted to products implicate the involvement of an ionic heterolytic bifunctional hydrogenation mechanism involving mutually cis Ir—H and N—H moieties, as illustrated in FIG. 2. The concerted outer sphere transfer of a hydride and NH proton to the carbonyl carbon and oxygen, respectively of the substrate resulted in the formation of the product and the highly reactive 16-electron amidodihydride species. Subsequent heterolytic activation of hydrogen gas resulted in the regeneration of the active trihydride catalyst.

In summary, this work in the present disclosure shows that iridium pincer aminodiphosphine complexes represent a very effective class of catalysts for hydrogenation of carbonyl substrates under very mild reaction conditions. It was also demonstrated that the series of chlorodihydride, trihydride and amidohydride iridium species represent an air-stable catalyst precursor, active catalyst, and putative intermediate, respectively. These species are analogous to the hydridochloro, dihydride and amidohydride ruthenium species of the Noyori catalysts.[4] It is unusual and rare to have a catalytic system that is equally effective and efficient for both hydrogenation and transfer hydrogenation,[6] but this class of iridium catalyst definitely fits this category.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

HYDROGENATION OF ACETOPHENONE IN METHANOL (10 ATM. $H_2$) AT ROOM TEMPERATURE.[a]

| entry | catalyst | S:C | time (h) | conv (%) |
|---|---|---|---|---|
| 1 | 2 | 1800 | 1 | 100 |
| 2 | 2 | 5000 | 5 | 100 |
| 3 | 1 | 1800 | 5 | 0 |
| 4 | 1/KO$^t$Bu | 1800 | 1 | 100 |
| 5 | 1/KO$^t$Bu | 5000 | 5 | 100 |

[a]A weighed amount of the catalyst was added to a solution of the substrate in methanol and the mixture stirred for the allotted time under hydrogen gas. The reaction progress was followed by NMR.

TABLE 2

HYDROGENATION OF ACETOPHENONE USING 1/KO$^T$BU (1:10) AS CATALYST IN VARIOUS SOLVENTS (10 ATM. $H_2$) AT ROOM TEMPERATURE.[a]

| entry | solvent | S:C | time (h) | conv (%) |
|---|---|---|---|---|
| 1 | methanol | 450 | 0.5 | 100 |
| 2 | ethanol | 450 | 1 | 100 |
| 3 | 2-propanol | 450 | 0.5 | 100 |
| 4 | ether | 450 | 1 | 100 |
| 5 | THF | 450 | 0.5 | 100 |
| 6 | Ethyl acetate | 450 | 0.5 | 100 |
| 7 | hexane | 450 | 0.5 | 100 |
| 8 | toluene | 450 | 1 | 100 |
| 9 | dichloromethane | 450 | 1 | 100 |
| 10 | chloroform | 450 | 1 | 100 |
| 11 | acetonitrile | 450 | 2 | 0 |

[a]A weighed amount of the catalyst was added to a solution of the substrate in the solvent and the mixture stirred for the allotted time under hydrogen gas. The reaction progress was followed by NMR.

TABLE 3

HYDROGENATION OF KETONES AND ALDEHYDES USING 1/KO$^T$BU (1:10) AS CATALYST IN METHANOL (10 ATM. $H_2$) AT ROOM TEMPERATURE.[a]

| Entry | substrate | S:C | time (h) | conv (%) |
|---|---|---|---|---|
| 1 | acetophenone | 900 | 1 | 100 |
| 2 | acetophenone | 6,000 | 5 | 100 |
| 3 | acetophenone | 30,000 | 12 | 100 |
| 4 | benzophenone | 500 | 1 | 100 |
| 5 | cyclohexanone | 1,100 | 1.5 | 100 |
| 6[b] | 4-tert-butylcyclohexanone | 700 | 1 | 100 |
| 7 | 2-butanone | 1,050 | 2 | 100 |
| 8 | 2-pentanone | 1,200 | 2 | 100 |
| 9 | 2-heptanone | 900 | 2 | 100 |
| 10 | 4-methyl-2-pentanone | 1,500 | 2 | 100 |
| 11 | pinacolone | 1,050 | 72 | 100 |
| 12 | 4-methoxyphenylacetone | 100 | 1 | 100 |

TABLE 3-continued

HYDROGENATION OF KETONES AND ALDEHYDES
USING 1/KO[T]BU (1:10) AS CATALYST
IN METHANOL (10 ATM. $H_2$) AT
ROOM TEMPERATURE.[a]

| Entry | substrate | S:C | time (h) | cony (%) |
|---|---|---|---|---|
| 13[c] | | 360 | 2 | 100 |
| 14[c] | | 300 | 1 | 100 |
| 15[d] | | 1,100 | 2 | 100 |
| 16 | | 250 | 2 | 100 |
| 17[e] | | 200 | 0.5 | 100 |
| 18[f] | | 600 | 2 | 100 |
| 19[g] | | 900 | 1 | 100 |
| 20 | | 1,000 | 2.5 | 100 |
| 21 | | 750 | 1.5 | 100 |

[a] A weighed amount of the catalyst (1/KO[t]Bu) was added to a solution of the substrate in methanol and the mixture stirred at room temperature under hydrogen gas. Yields are based on the amount of substrate.
[b] Ratio of cis:trans alcohol = 1:2;
[c] only carbonyl group is reduced;
[d] ratio of saturated:allyl alcohol = 1:1;
[e] ratio of meso:rac alcohol = 3:1;
[f] rac-alcohol is the only product;
[g] ratio of endo:exo = 6:1.

FULL CITATIONS FOR DOCUMENTS REFERRED TO IN THE SPECIFICATION (1)(a) Mikami, K.; Korenaga, T.; Terada, M.; Ohkuma, T.; Pham, T.; Noyori, R. *Angew. Chem., Int. Ed.* 1999, 38, 495-497. (b) Doucet, H.; Ohkuma, T.; Murata, K.; Yokozawa, T.; Kozawa, M.; Katayama, E.; England, A. F.; Ikariya, T.; Noyori, R. *Angew. Chem., Int. Ed.* 1998, 37, 1703-1707. (c) Ohkuma, T.; Ooka, H.; Ikariya, T.; Noyori, R. *J. Am. Chem. Soc.* 1995, 117, 10417-10418.

(2)(a) Ohkuma, T.; Koizumi, M.; Doucet, H.; Pham, T.; Kozawa, M.; Murata, K.; Katayama, E.; Yokozawa, T.; Ikariya, T.; Noyori, R. *J. Am. Chem. Soc.* 1998, 120, 13529-13530. (b) Ohkuma, T.; Doucet, H.; Pham, T.; Mikami, K.; Korenaga, T.; Terada, M.; Noyori, R. *J. Am. Chem. Soc.* 1998, 120, 1086-1087. (c) Ohkuma, T.; Ooka, H.; Yamakawa, M.; Ikariya, T.; Noyori, R. *J. Org. Chem.* 1996, 61, 4872-4873.

(3)(a) Abdur-Rashid, K.; Lough, A. J.; Morris, R. H. *Organometallics* 2001, 20, 1047-1049. (b) Abdur-Rashid, K.; Lough, A. J.; Morris, R. H. *Organometallics* 2000, 19, 2655-2657.

(4)(a) Abbel, R.; Abdur-Rashid, K.; Faatz, M.; Hadzovic, A.; Lough, A. J.; Morris, R. H. *J. Am. Chem. Soc.* 2005, 127, 1870-1882. (b) Abdur-Rashid, K.; Clapham, S. E.; Hadzovic, A.; Lough, A. J.; Morris, R. H. *J. Am. Chem. Soc.* 2002, 124, 15104-15118. (c) Abdur-Rashid, K.; Faatz, M.; Lough, A. J.; Morris, R. H. *J. Am. Chem. Soc.* 2001, 123, 7473-7474.

(5) Clarke, Z. E.; Maragh, P. T.; Dasgupta, T. P.; Gusev, D. G.; Lough, A. J.; Abdur-Rashid, K. *Organometallics* 2006, 25, 4113-4117.

We claim:

1. A method for the reduction of compounds comprising one or more carbon-oxygen (C=O) double bonds comprising contacting the compound with hydrogen gas and a catalyst comprising an iridium aminodiphosphine complex and a base, wherein the hydrogen gas is used at a pressure greater than 3 atm and the complex is of the formula (II):

$$IrX_3[P_2NH] \qquad (II)$$

wherein

X may be the same or different and are selected from hydrogen and any anionic ligand;

[$P_2NH$] represents a tridentate aminodiphosphine ligand of formula (III):

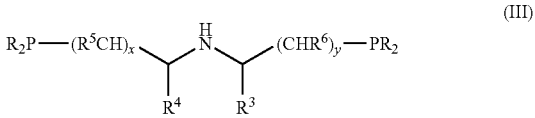

(III)

in which $R^3$ to $R^6$ simultaneously or independently are selected from of H, $C_{1-20}$alkyl, $C_{2-20}$alkenyl, $C_{3-20}$cycloalkyl and aryl, said latter 4 groups being optionally substituted, or two adjacent or geminal $R^3$, $R^4$, $R^5$ or $R^6$ groups are bonded together to form an optionally substituted ring;

x and y are, simultaneously or independently, equal to 0, 1, 2, 3 or 4; and

R is simultaneously or independently selected from H, $C_{1-20}$alkyl, aryl and $C_{2-20}$alkenyl, $OR^d$ and $NR^d_2$, said latter 5 groups being optionally substituted, or the R groups on the same P atom are linked together to form an optionally substituted monocyclic or polycyclic, saturated, unsaturated and/or aromatic ring system having 4 or more atoms, including the phosphorous atom to which said R groups are bonded, and in which one or more carbon atoms in said ring system is optionally replaced with a heteromoiety selected from O, S, N, NH, NC$_{1-6}$alkyl and Si;

the optional substituents are selected from one or more of halo, OH, NH$_2$, OR$^d$, NR$^d_2$ and R$^d$;

R$^d$ is selected from C$_{1-6}$alkyl, C$_{2-6}$alkenyl, C$_{3-10}$cycloalkyl and aryl, wherein one or more of the carbon atoms in the alkyl, alkenyl, cycloalkyl and aryl groups is optionally replaced with a heteromoiety selected from O, S, N, NH, NC$_{1-6}$alkyl and Si and one or more of the hydrogen atoms in the alkyl, alkenyl, cycloalkyl and aryl groups is optionally replaced with F.

2. The method according to claim 1, wherein the compound comprising a carbon-oxygen (C=O) double bond is a compound of formula (I):

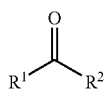

wherein,
R$^1$ and R$^2$ each simultaneously or independently are selected from H, aryl, C$_{1-20}$alkyl, C$_{2-20}$alkenyl, C$_{3-20}$cycloalkyl and heteroaryl, said latter 5 groups being optionally substituted, or R$^1$ and R$^2$ are linked to form an optionally substituted ring;

wherein heteroaryl is a mono- bi or tricyclic heteroaromatic radical containing from 5 to 14 atoms, of which 1-5 atoms is a heteromoiety selected from S, O, N, NH and NC$_{1-6}$alkyl and wherein the optional substituents are selected from one or more of =O, halo, OH, NH$_2$, OR$^c$, NR$^c_2$ and R$^c$, in which R$^c$ is selected from C$_{1-6}$alkyl, C$_{2-6}$alkenyl, C$_{3-10}$cycloalkyl and aryl and one or more of the carbon atoms in the alkyl, alkenyl cycloalkyl and aryl groups is optionally replaced with a heteromoiety selected from O, S, N, NH, NC$_{1-6}$alkyl, P and Si and one or more of the hydrogen atoms in the alkyl, alkenyl, cycloalkyl and aryl groups is optionally replaced with F.

3. The method according to claim 2, wherein R$^1$ and R$^2$ are different.

4. The method according to claim 3, wherein in the tridentate ligand of formula III, R$^3$ to R$^6$ simultaneously or independently are selected from H, C$_{1-10}$alkyl, C$_{2-10}$alkenyl, C$_{3-10}$cycloalkyl and aryl, said latter 4 groups being optionally substituted, or two adjacent or geminal R$^3$, R$^4$, R$^5$ and R$^6$ groups are bonded together to form an optionally substituted ring.

5. The method according to claim 4, wherein R$^3$ to R$^6$ simultaneously or independently are selected from H, C$_{1-4}$alkyl, C$_{2-4}$alkenyl, C$_{3-6}$cycloalkyl and aryl, said latter 4 groups being optionally substituted, or two adjacent or geminal R$^3$, R$^4$, R$^5$ and R$^6$ groups are bonded together to form an optionally substituted ring, said ring containing 6 atoms, including the carbons to which said groups are attached.

6. The method according to claim 5, wherein R$^3$, R$^4$, R$^5$ and R$^6$ are all H.

7. The method according to claim 3, wherein in the tridentate ligand of formula III, x and y are simultaneously equal to 0, 1, 2, 3 or 4.

8. The method according to claim 7, wherein x and y are simultaneously equal to 0, 1 or 2.

9. The method according to claim 8, wherein x and y are simultaneously equal to 1.

10. The method according to claim 3, wherein in the tridentate ligand of formula III, R is simultaneously or independently selected from H, C$_{1-10}$alkyl, aryl and C$_{2-10}$alkenyl, said latter 3 groups being optionally substituted, or the R groups on the same P atom are linked together to form an optionally substituted monocyclic or polycyclic ring system having 4 or more atoms, including the phosphorous atom to which said R groups are bonded, which is saturated, unsaturated and/or aromatic and in which one or more carbon atoms in said monocyclic or polycyclic ring system is optionally replaced with a heteromoiety selected from O and NH.

11. The method according to claim 10, wherein R is simultaneously or independently selected from H, C$_{1-6}$alkyl, phenyl, naphthyl and C$_{2-6}$alkenyl, said latter 4 groups being optionally substituted, or the R groups on the same P atom are linked together to form an optionally substituted monocyclic, fused bicylic, fused tricyclic, fused quadracyclic or fused pentacyclic ring system having 4-23 atoms, including the phosphorous atom to which said R groups are bonded, which is saturated, unsaturated and/or aromatic and in which one or more carbon atoms in said monocyclic or polycyclic ring system is optionally replaced with a heteromoiety selected from O and NH.

12. The method according to claim 11, wherein R is simultaneously C$_{1-6}$alkyl or phenyl.

13. The method according to claim 3, wherein the two R groups on each phosphorus atom are linked to form a monocyclic saturated ring containing from 4 to 7 atoms, including the phosphorus atom to which the R groups are attached, said ring being optionally substituted with 1 to 2 substituents independently selected from fluoro-substituted-C$_{1-6}$alkyl, C$_{1-6}$alkyl, C$_{2-6}$alkenyl and aryl, and wherein one or two of the carbon atoms in the ring is optionally replaced with a heteromoiety selected from O, S and N—C$_{1-4}$alkyl.

14. The method according to claim 13, wherein the monocyclic saturated ring contains 4-5 atoms, including the phosphorus atom to which the R groups are attached.

15. The method according to claim 13, wherein the substituents are independently selected from C$_{1-4}$alkyl, C$_{2-4}$alkenyl and phenyl.

16. The method according to claim 15, wherein the substituents are independently selected from methyl and phenyl.

17. The method according to claim 13, wherein the optional heteromoieties or optional substituents are located at positions alpha to the phosphorus atom.

18. The method according to claim 4, wherein the two R groups on the phosphorus atom are linked to form a polycyclic ring system comprising 3, 5 or 7 rings each ring being fully saturated, partially unsaturated and/or aromatic and which are optionally substituted with 1 to 2 substituents independently selected from fluoro-substituted-C$_{1-6}$alkyl, C$_{1-6}$alkyl, C$_{2-6}$alkenyl and aryl, and wherein one or two of the carbon atoms in the ring may be replaced with a heteromoiety selected from O, S and N—C$_{1-4}$alkyl.

19. The method according to claim 18, wherein the optional substituents are independently selected from C$_{1-4}$alkyl, C$_{2-4}$alkenyl and phenyl.

20. The method according to claim 19, wherein the optional substituents are independently selected from methyl or phenyl.

21. The method according to claim 20, wherein one or two of the carbon atoms in the ring may be replaced with a heteromoiety selected from O and N—CH$_3$.

22. The method according to claim 18, wherein the optional heteromoieties or optional substituents are located at positions alpha to the phosphorus atom.

23. The method according to claim 3, wherein both phosphorus atoms in the compounds of Formula II are identically substituted.

24. The method according to claim 3, wherein the optional substituents on the compounds of formula III are selected from one or more of halo, OH, $NH_2$, $OR^d$, $NR^d_2$ and $R^d$, in which $R^d$ is selected from fluoro-substituted-$C_{1-4}$alkyl, $C_{1-4}$alkyl, $C_{2-4}$alkenyl and phenyl.

25. The method according to claim 3, wherein the groups $R^3$, $R^4$, $R^5$ and $R^6$ and R in the ligands of Formula III are unsubstituted.

26. A method for the reduction of compounds comprising one or more carbon-oxygen (C=O) double bonds comprising contacting the compound with hydrogen gas and a catalyst comprising an iridium aminodiphosphine complex, wherein the hydrogen gas is used at a pressure greater than 3 atm and the complex is of the formula (IV)

$$IrH_3[P_2NH] \quad (IV)$$

wherein
[$P_2NH$] is as defined in claim 1.

27. The method according to claim 26, wherein the activated iridium complex (IV) is prepared in situ, without isolation or purification, just before its use.

28. The method according to claim 1, wherein the base is an organic non-coordinating base, an alkaline or alkaline-earth metal carbonate, a carboxylate salt or an alcoholate or hydroxide salt.

29. The method according to claim 28, wherein the base is an alcoholate or a hydroxide salt selected from compounds of formula $(R^7O)_2M'$ and $R^7OM''$, in which M' is an alkaline-earth metal, M" is an alkaline metal and $R^7$ is hydrogen or $C_{1-10}$alkyl.

30. The method according to claim 29, wherein $R^7$ is t-butyl and M" is potassium.

31. The method according to claim 1, wherein the solvent is selected from benzene, toluene, xylene, hexane, cyclohexane, tetrahydrofuran, diethyl ether, primary or secondary alcohols, chlorinated solvents and mixtures thereof.

32. The process according to claim 1, wherein the hydrogen gas is used at a pressure in the range of about 7 atm to about 13 atm.

33. The process according to claim 26, wherein the hydrogen gas is used at a pressure in the range of about 7 atm to about 13 atm.

* * * * *